(12) United States Patent
Madsen et al.

(10) Patent No.: US 6,602,219 B2
(45) Date of Patent: *Aug. 5, 2003

(54) TURBULENT AIR CLEANING METHOD AND APPARATUS FOR CATHETER ASSEMBLIES

(75) Inventors: Edward B. Madsen, Riverton, UT (US); Wayne D. Carlsen, West Jordan, UT (US); Chet M. Crump, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 21 days.

This patent is subject to a terminal disclaimer.

(21) Appl. No.: 09/741,769

(22) Filed: Dec. 19, 2000

(65) Prior Publication Data

US 2002/0077586 A1 Jun. 20, 2002

(51) Int. Cl.[7] .............................................. A61M 1/00
(52) U.S. Cl. ..................... 604/27; 604/267; 128/207.29
(58) Field of Search ................................ 604/523–539, 604/266, 267, 27, 28, 35; 128/207.14, 207.29

(56) References Cited

U.S. PATENT DOCUMENTS

| 3,991,762 A | * | 11/1976 | Radford | 128/276 |
|---|---|---|---|---|
| 4,569,344 A | | 2/1986 | Palmer | |
| 5,060,646 A | | 10/1991 | Page | |
| 5,073,164 A | | 12/1991 | Hollister et al. | |
| 5,140,983 A | * | 8/1992 | Jinotti | 128/207.14 |
| 5,254,098 A | | 10/1993 | Ulrich et al. | |
| 5,333,606 A | | 8/1994 | Schneider et al. | |
| 5,343,857 A | | 9/1994 | Schneider et al. | |
| 5,349,950 A | | 9/1994 | Ulrich et al. | |
| 5,445,141 A | | 8/1995 | Kee et al. | |
| 5,487,381 A | | 1/1996 | Jinotti | |
| 5,490,503 A | | 2/1996 | Hollister | |
| 5,513,628 A | * | 5/1996 | Coles et al. | 128/200.26 |
| 5,664,594 A | * | 9/1997 | Kee | 134/22.11 |
| 5,711,294 A | * | 1/1998 | Kee et al. | 128/202.27 |
| 6,227,200 B1 | * | 5/2001 | Crump et al. | 128/207.16 |

FOREIGN PATENT DOCUMENTS

| EP | 0345228 | 12/1989 |
|---|---|---|
| WO | 0015276 | 3/2000 |

OTHER PUBLICATIONS

U.S. patent application No. 09/357,591, filed Jul. 20, 1999 (BAL–66–CIP).
U.S. patent application No. 09/702,375, filed Oct. 31, 2000 (BAL–54).
U.S. patent application No. 09/693,261, filed Oct. 20, 2000 (BAL–66–CIP–CON).
U.S. patent application No. 09/716,786, filed Nov. 20, 2000 (BAL–66–CON).
EPO Search Report, Nov. 8, 2002.

* cited by examiner

Primary Examiner—Timothy S. Thorpe
Assistant Examiner—Han L. Liu
(74) Attorney, Agent, or Firm—Dority & Manning

(57) ABSTRACT

A method and apparatus are provided for cleaning a medical device tube, for example a catheter tube. The distal end portion of the tube has a distal opening and at least one side opening adjacent to the distal opening. The distal end of the tube is disposed in a closed chamber with the distal opening generally opposite from a first orifice defined in the chamber. A liquid is introduced into the chamber and is drawn into the distal opening in the tube, for example by a suction force. A different fluid medium, such as air, is drawn through the first orifice and into the distal opening in the tube. A turbulent flow path is established with the fluid medium wherein the medium is drawn through the first orifice, into the distal opening in the tube, out the side opening in the tube, and back into the distal opening in the tube. This turbulent flow path enhances the cleaning action of the liquid introduced into the chamber for cleaning the distal end portion of the tube within the chamber.

34 Claims, 7 Drawing Sheets

TURBULENT AIR CLEANING METHOD AND APPARATUS FOR CATHETER ASSEMBLIES

BACKGROUND OF THE INVENTION

There are a number of different circumstances in which it is necessary for a person to have an artificial airway placed in his or her respiratory tract. As used herein, the phrase "artificial airway" includes devices such as tracheostomy tubes, endotracheal tubes, and the like. An artificial airway keeps the patient's natural airway open so that adequate lung ventilation can be maintained.

In certain situations, the artificial airway must be left in the patient for a prolonged period of time. In these situations, it is critical that respiratory secretions be periodically removed from the patient's respiratory tract. This is typically accomplished by the use of a respiratory suction catheter.

With conventional closed suction catheter assemblies, for example as set forth in U.S. Pat. Nos. 3,991,762 and 4,569,344, the catheter tube is enveloped by a protective sleeve. The catheter assembly includes a valve mechanism in communication with a vacuum source to control the suctioning process. At its distal or patient end, the closed suction catheter assembly is attached to the artificial airway via a manifold, connector, adaptor, or the like. When it is desired to remove secretions and mucous from the patient's respiratory tract, the catheter tube is advanced through the protective sleeve and into the patient's respiratory system through the artificial airway. Negative pressure is then applied to the proximal or clinician end of the catheter tube to evacuate the secretions and mucous. The tube is then withdrawn from the artificial airway and, as the catheter tube is pulled back into the protective sleeve, a wiper or seal strips or scrapes a substantial portion of any mucous or secretions from the outside of the catheter tube. However, the distal tip portion of the catheter tube does not pass through the seal or wiper and thus any secretions or mucous on the distal end must be removed by other means.

Some closed suction catheter assemblies typically include a lavage port for injecting a cleaning/lavage solution into a chamber at the distal end of the catheter assembly as suction is applied through the catheter tube for loosening and removing the secretions and mucous scraped from the exterior of the catheter tube. This procedure may be done with the catheter assembly attached to or removed from the artificial airway and the ventilation circuit.

In certain situations, the lavage injection and suctioning process may not adequately remove the secretions and mucous adhering to the distal tip of the catheter tube and the clinician may repeat the cleaning process a number of times in an attempt to clean the catheter tip. If the mucous and secretions accumulate or dry on the catheter tip, they can interfere with the suction efficiency of the catheter and necessitate premature replacement of the entire closed suction catheter assembly.

It may also be desired to remove any cleaning/lavage solution that may remain in the lavage chamber after the cleaning procedure before using the device again.

Thus, there is a need for a suction catheter assembly having a more efficient mechanism and method for adequately cleaning a catheter tube of a suction catheter assembly.

SUMMARY OF THE INVENTION

Objects and advantages of the invention will be set forth in part in the following description, or may be obvious from the description, or may be learned through practice of the invention.

As used herein, the term "distal" refers to the direction of the patient and the term "proximal" refers to the direction of the clinician.

The present invention relates to a method and apparatus for creating a turbulent fluid flow at an end of a tube having a distal opening and one or more side openings adjacent to the distal opening. It is believed that such a turbulent flow may have numerous beneficial applications in various fields in mixing procedures, cleaning procedures, etc. The invention has particular usefulness in the medical field. For example, in one particularly well suited application of the invention, the turbulent flow significantly enhances cleaning of the distal end portion of a suction catheter. It is also contemplated that the turbulent flow may be useful in other applications, including mixing, heating, or cooling solutions. It should thus be appreciated that the present method and apparatus are not limited to any particular type or configuration of medical device or intended use.

The method includes disposing the distal end portion of the medical tube in a closed chamber having a first orifice defined therethrough. The orifice is disposed in the chamber so as to be generally opposite from the tube. A liquid, such as a lavage or cleaning solution, is introduced into the chamber. The liquid is drawn into the distal opening in the tube, for example by applying a suction through the tube. As the liquid is drawn into the distal opening, another fluid medium, such as air, is drawn into the chamber through the first orifice. Applicants believe that a flow pattern is established wherein the fluid medium is drawn through the orifice and into the distal opening in the tube with the liquid. A portion of the fluid/liquid mixture drawn into the tube is conveyed out the side opening(s) in the tube, and back into the distal opening in the tube. This flow pattern may create a turbulence in the lavage or cleaning solution within the chamber, particularly around the circumference of the tube and within the distal end portion of the tube. It has been found that this turbulence creates a significant advantage in cleaning the distal end portion of the tube. For example, in an embodiment wherein the medical tube is a suction catheter tube, the turbulent air flow assists in breaking up conglomerations of mucous and secretions which the lavage/cleaning solution alone may not.

In the embodiment wherein the medical device tube is a catheter tube, particularly a suction catheter tube, the distal end portion of the tube may be withdrawn into a distal fitting such as an adaptor or manifold housing of the respective catheter assembly. "Fitting" is a relatively broad term used to encompass any structure located at the distal end of the catheter assembly through which the catheter tube is withdrawn and includes, for example, any configuration of adaptor, connector, manifold, extension, etc. The fitting thus defines at least in part a portion of the closed chamber. The closed chamber may be considered as a cleaning chamber.

Once the distal end portion of the catheter tube is withdrawn into the fitting, a cover member is used to close off or seal the cleaning chamber. The first orifice may be defined through this cover member.

In one embodiment, the fitting may comprise an adaptor having a port that is detachable from a patient's artificial airway, such as a tracheostomy tube, endotracheal tube, and the like. In this embodiment, the cover member may be a component separate from the adaptor that is configured to then be attached to the adaptor to close off the port once the distal end portion of the catheter tube has been withdrawn into the adaptor. The cover member cooperates with the adaptor to define the cleaning chamber in which the distal end portion of the catheter tube is disposed.

In an alternate embodiment, the cover member may be connected to and disposed within the fitting, particularly in the adaptor embodiment of the invention. The catheter tube is withdrawn into the adaptor past the cover member which then moves automatically to a sealing position once the distal end of the catheter tube has passed the cover member. For example, in this embodiment, the cover member may comprise a hinged flap member that moves into a position generally opposite from the distal end of the catheter tube once the catheter tube has been withdrawn past the flap member.

Once the distal end portion of the catheter tube is properly located within the cleaning chamber and the cover member has been positioned so that the first orifice is generally opposite from the distal opening in the tube, the turbulent flow process is initiated as described above. In the embodiment of the invention wherein the catheter tube is a respiratory suction catheter, suction is applied at the proximal end of the tube to draw the cleaning solution into the tube. This suction also establishes a vacuum condition within the cleaning chamber resulting in air being drawn through the first orifice into the cover member. In an alternate embodiment, the air introduced through the first orifice may be pressurized air.

In a cleaning operation as described herein, it may be desired to remove any remaining cleaning solution from the cleaning chamber prior to reusing the respiratory suction catheter. The cleaning solution is typically removed by suctioning the solution from the chamber through the distal opening of the catheter tube. However, with relatively larger cleaning chambers, it is possible that not all of the cleaning solution may be removed. Accordingly, the method and apparatus according to the invention may include additional steps and structure to ensure adequate removal of the cleaning solution from the cleaning chamber.

In one embodiment, additional orifices or holes are defined in the cleaning chamber and are disposed so as to direct the fluid medium, such as air, into the cleaning chamber at an angle and orientation so as to urge the lavage/cleaning solution away from the sides of the cleaning chamber and towards the distal opening in the catheter tube. After air is drawn through the first orifice for a period of time sufficient for cleaning the distal end portion of the catheter tube, the air or other fluid medium is then introduced through the additional orifices. In one embodiment, the additional orifices are a ring of orifices disposed around the first orifice. The additional orifices are covered by a separate cover device or cap.

The invention will be described in greater detail below with reference to various embodiments depicted in the figures.

DETAILED DESCRIPTION

Figure 1:
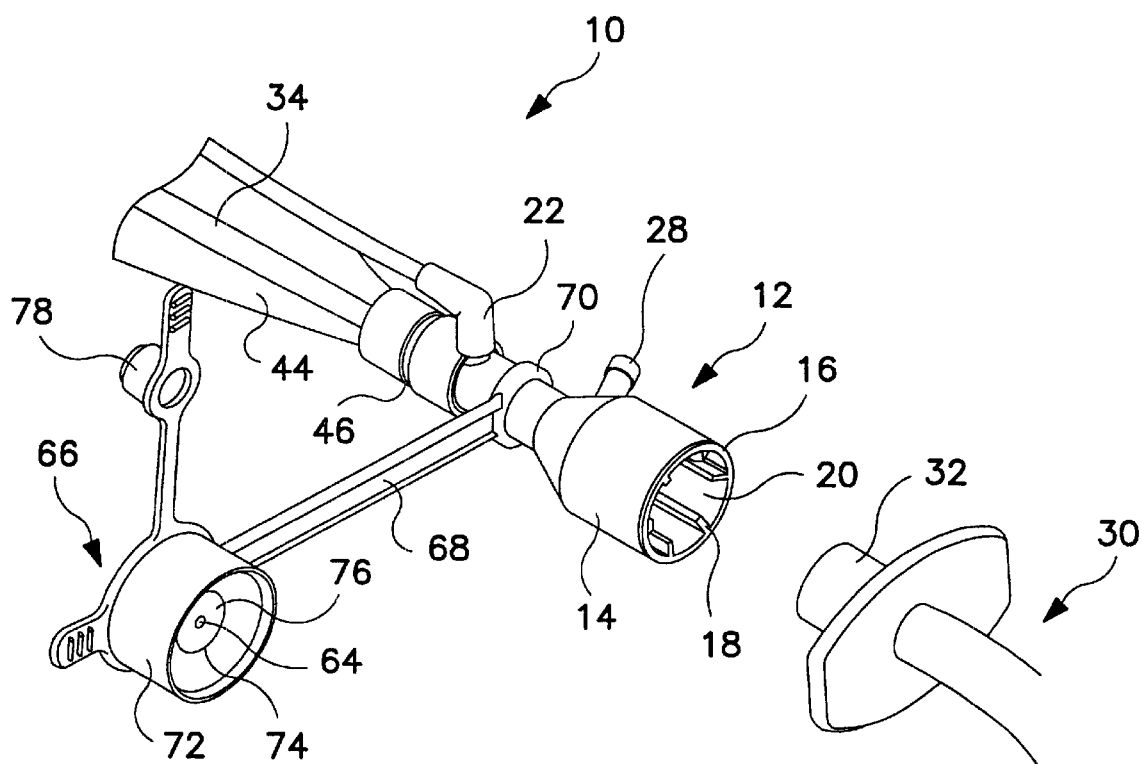
FIG. 1 is a partial perspective view of a catheter assembly according to the present invention.

Reference will now be made in detail to embodiments of the invention, one or more examples of which are shown in the drawings. It should be appreciated that each example is provided by way of explaining the invention, and not as a limitation of the invention. For example, features illustrated or described with respect to one embodiment may be used with another embodiment to yield still a further embodiment. These and other modifications and variations are within the scope and spirit of the invention.

The method and apparatus for creating turbulent flow conditions at the distal end of a tube will be described with reference to a medical device embodiment of the invention, particularly a catheter assembly embodiment depicted in the figures. It should be appreciated, however, that the method and apparatus of the present invention are not limited to the catheter assemblies shown, or the medical field in general. The method and apparatus may be utilized in any device wherein it is desired to create turbulent flow conditions for any number of reasons, including cleaning a tube or other device, mixing fluids, heating or cooling solutions, etc.

Figure 2:
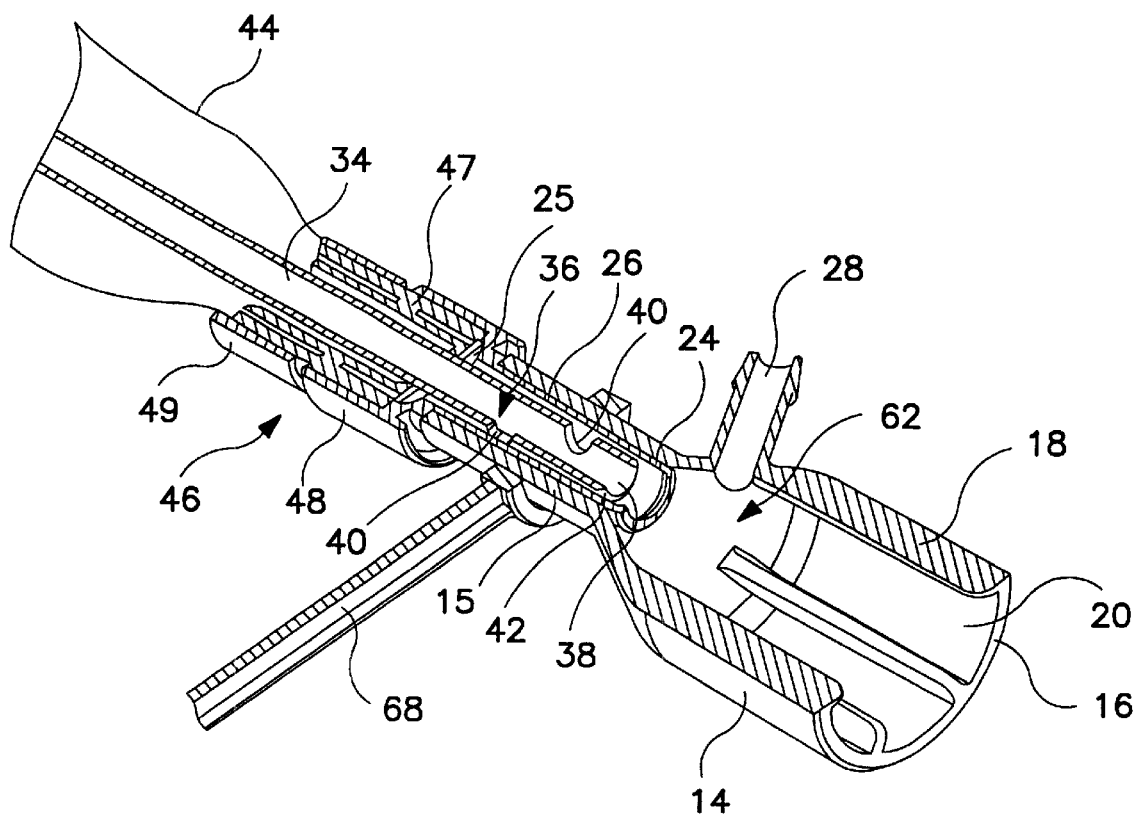
FIG. 2 is a cross-sectional view of the distal portion of the catheter assembly of FIG. 1.

Referring to FIGS. 1 and 2 in particular, a catheter assembly 10 is illustrated, particularly a respiratory suction catheter assembly utilizing a suction catheter tube 34 having a distal end portion 36. The distal end portion 36 includes a distal opening 38 defined in an extreme distal tip 42 of the catheter tube and at least one lateral or side opening 40 disposed adjacent to the distal tip 42. The use of a respiratory suction catheter to remove secretions and mucous from a patient's respiratory tract is well known by those skilled in the art and need not be explained in detail herein. The turbulent flow method and apparatus according to the present invention is particularly useful for cleaning accumulated secretions and mucous from the distal end portion 36 of the catheter tube 34 and, thus, the respiratory catheter suction assembly is useful for explaining the present invention.

A fitting 12 is provided at the distal end of the catheter assembly. The term "fitting" is used herein as a broad generic term that encompasses any structure provided at the distal end of the catheter assembly 10 and may include, for example, an adaptor 14 as illustrated in the figures. Referring to FIGS. 1 and 2, the adaptor 14 is particularly configured for connecting with a hub or manifold 32 of a patient's artificial airway 30. The artificial airway 30 may be, for example, a tracheostomy tube, endotracheal tube, or the like. The adaptor 14 includes a side wall 16 defining a port 20 that communicates with the hub 32 of the artificial airway 30. Radially projecting ribs 18 may be defined on the inner circumference of the wall 16 to ensure adequate airflow between the wall 16 and the hub 32. The adaptor 14 may include one or more additional ports 28 for providing access through the adaptor 14 to the patient's respiratory tract. It should be appreciated that the particular configuration of the adaptor 14 illustrated in the figures is not a limiting feature of the invention. The adaptor may take on any desired form or configuration.

Figure 4:
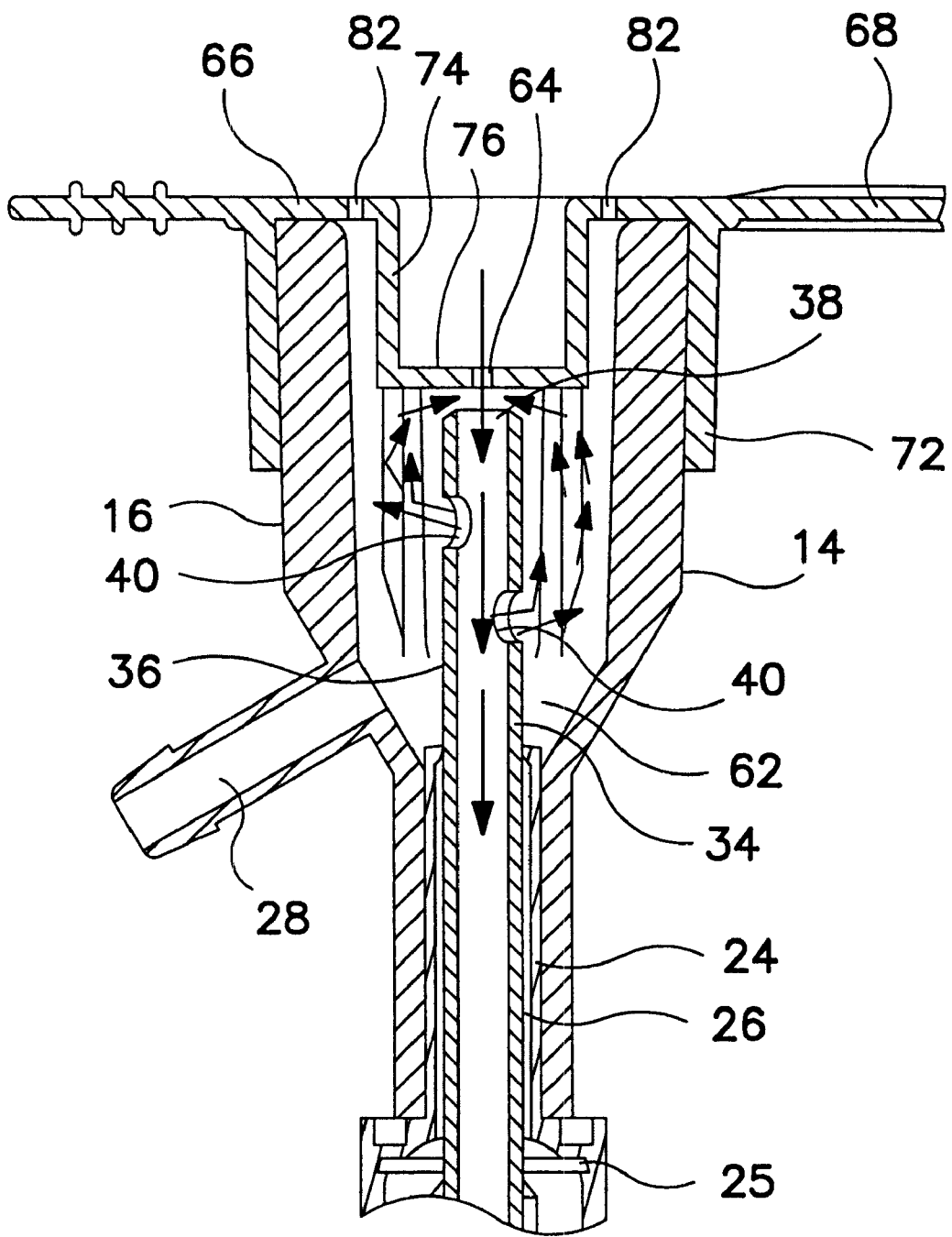
FIG. 4 is a cross-sectional operational view of the distal end of a catheter assembly according to the invention.

The adaptor 14 configuration of FIGS. 1, 2, and 4 is also described in detail in co-pending and commonly owned U.S. patent application Ser. No. 09/702,375 filed on Oct. 31, 2000. The '375 application is incorporated herein by reference in its entirety for all purposes.

The catheter assembly 10 may also include various configurations of the distal structure 46 for interconnecting the components of the catheter assembly 10. For example, referring to FIG. 2, the distal end structure 46 may include a connection member 47. A fitting 48 may be connected to the distal portion of member 47, the fitting 48 including a longitudinally extending collar 24 having an inner diameter slightly greater than the outer diameter of the catheter tube 34 such that an annular space 26 is defined between the components, as particularly seen in FIG. 2. A wiper seal 25 may be disposed at the proximal end of the annular space 26 for cleaning the distal portion 36 of the catheter tube 34 as the tube is withdrawn through the collar 24. The adaptor 14 may be pressed onto, adhered, or otherwise connected to the outer surface of the collar 24. Another fitting 49 may be pressed onto, adhered to, or otherwise attached to the opposite end of connection member 47. The fitting 49 may be used, for example, to secure a sleeve 44 to the catheter assembly 10. As is well known by those skilled in the art, the catheter tube 34 is slidable through the sleeve, distal structure 46, and adaptor 14 to be inserted into and withdrawn from the patient's respiratory tract through the artificial airway 30. It should be appreciated that the configuration of the distal structure 46 illustrated in the figures is but one example of any number of suitable configurations.

A method according to the invention includes disposing the distal end portion 36 of the catheter tube 34 in a closed chamber. In the illustrated embodiments, the closed chamber is a cleaning chamber 62 defined at least in part by the fitting 12, and particularly within the adaptor 14. As will be explained in greater detail below, the chamber may be "closed" by a suitable cover member once the catheter tube 34 has been withdrawn into the cleaning chamber 62.

Figure 5:
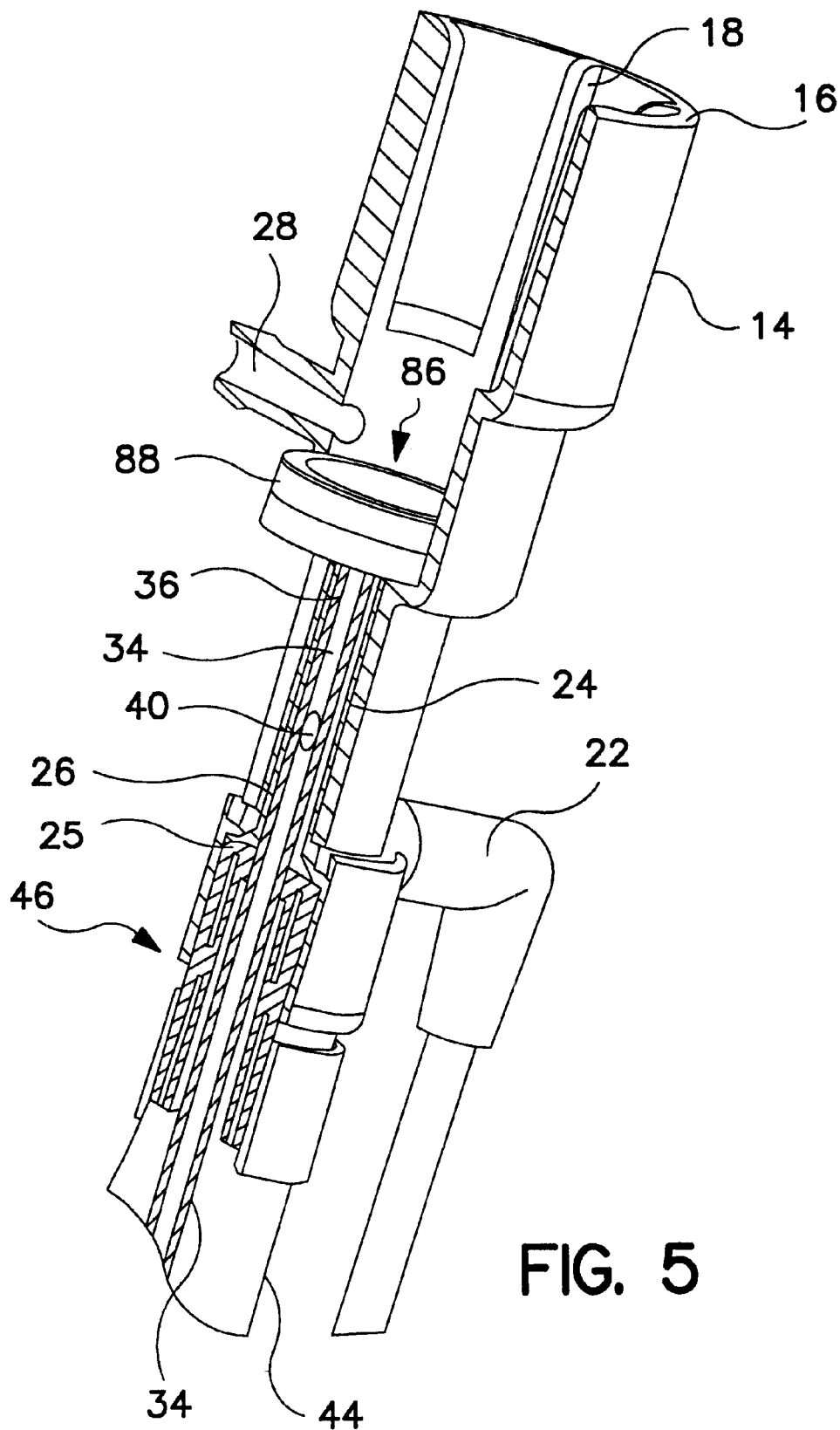
FIG. 5 is a perspective and partial cross-sectional view of an alternate embodiment of a catheter assembly according to the invention.
Figure 6:
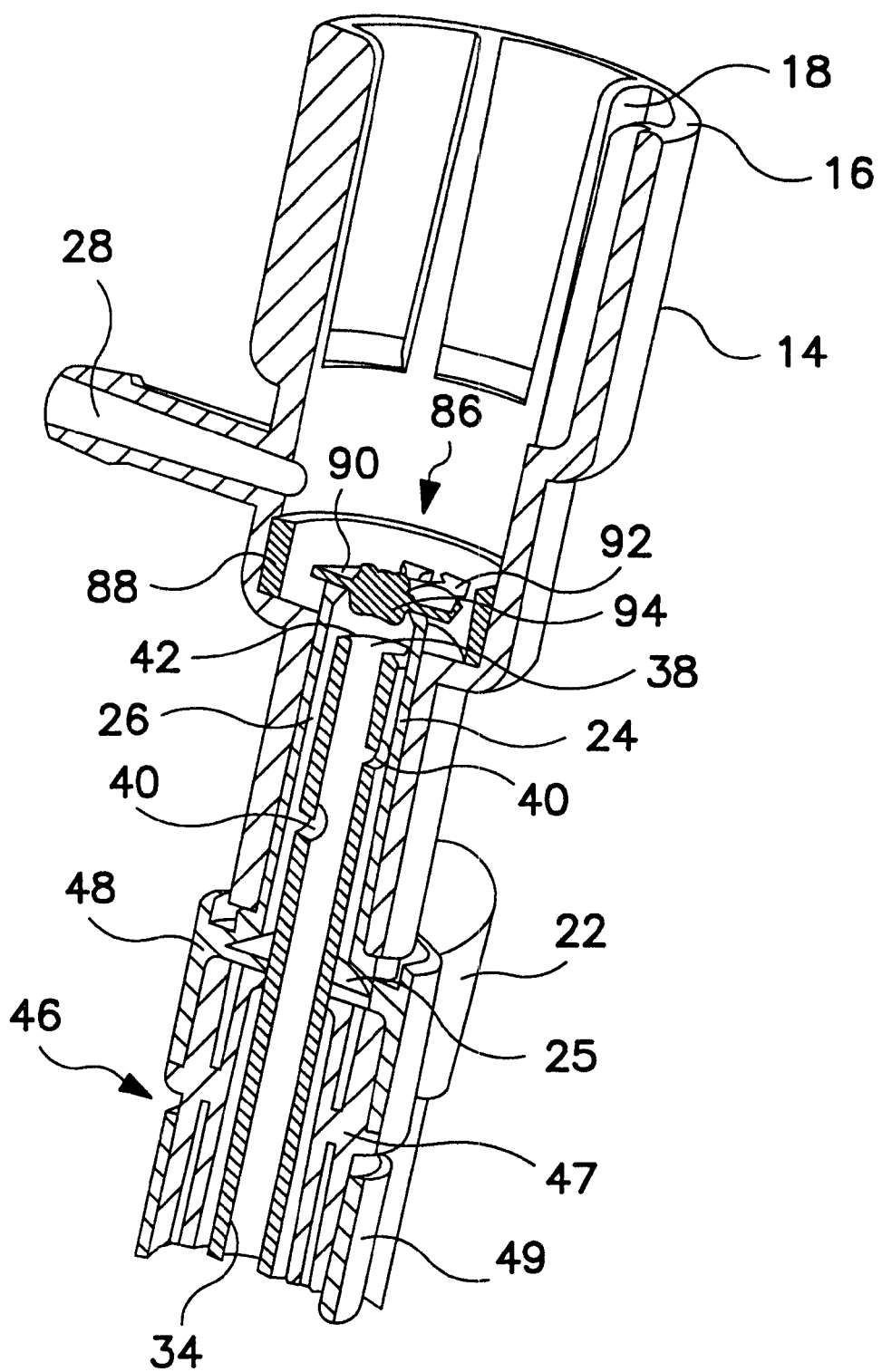
FIG. 6 is an alternate cross-sectional view of the catheter assembly embodiment of FIG. 5.

The chamber 62 has at least one orifice 64. This orifice 64 is may be located so as to be generally opposite and spaced from the distal opening 38 of the catheter tube 34. In the illustrated embodiments, the orifice 64 is defined in an external cover member 66 or internal cover member 86 (FIGS. 5 and 6).

Figure 3:
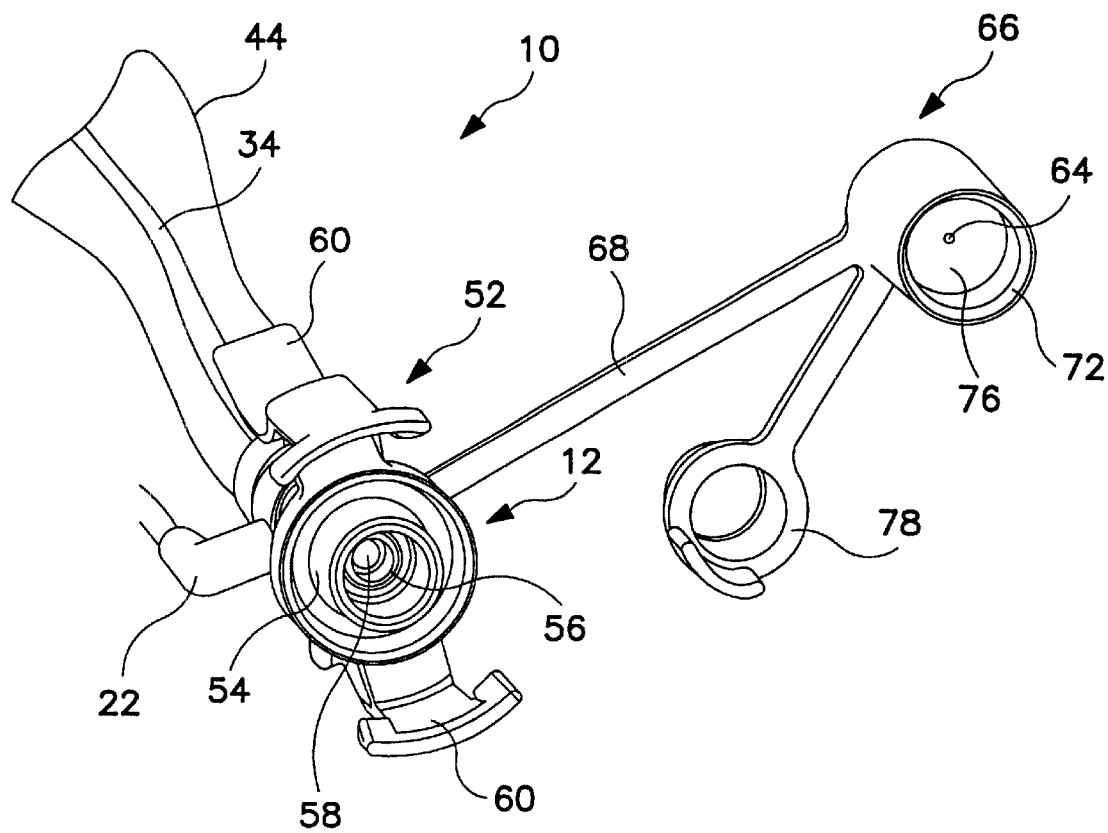
FIG. 3 is a perspective view of a distal portion of another embodiment of a catheter assembly according to the present invention.

FIG. 3 illustrates an alternative catheter assembly 10 that incorporates a heat and moisture exchanger (HME) adaptor 52 at the distal end of the catheter assembly 10. Various configurations and operation of the HME adaptor 52 are described in detail in co-pending and commonly owned U.S. patent application Ser. No. 09/702,376 filed on Oct. 31, 2000. The '376 application is incorporated herein in its entirety for all purposes. In general, the HME adaptor 52 may be disposed at the distal end of a closed suction catheter assembly for receipt of a removable heat and moisture exchange device. In this embodiment, the HME adaptor 52 corresponds to the "fitting" structure that defines at least in part the cleaning chamber 62. The HME adaptor 52 may include a first cylindrical wall 54 configured for engagement with a removable HME device. A second cylindrical wall 56 defines a channel 58 through which the catheter tube 34 is slidably disposed. The catheter tube 34 may be advanced through the HME adaptor 52 and attached HME device into the patient's respiratory tract through the artificial airway 30, as described in detail in the co-pending '376 application.

Embodiments of the external cover member 66 are illustrated in FIGS. 1, 3, 4, and 7. The cover member 66 has a shape and configuration so as to seal or close the distal end of the adaptor 14 or HME adaptor 52 (FIG. 3). Once the clinician removes the catheter assembly 10 from the hub 32 of the artificial airway 30, the cover member is placed over the port 20 to define a closed chamber (cleaning chamber) 62. The cover member 66 may be attached to any portion of the catheter assembly 10, including by way of an attaching arm 68. For example, a ring 70 may be provided at the end of the arm 68 for securing the cover member 66 to the catheter assembly 10. The cover member 66 may include any appropriate structure for closing or sealing the end of the fitting structure 12. For example, the cover member 66 may include a cylindrical wall 72 that engages at lest a portion of the outer circumference of the cylindrical wall 16 of the adaptor 14, as particularly seen in FIG. 4. Likewise, referring to FIG. 3, the cylindrical wall 72 may be sized so as to fit within the first cylindrical wall 54 of the HME adaptor 52 and engage at least a portion of the second cylindrical wall 56.

Figure 7:
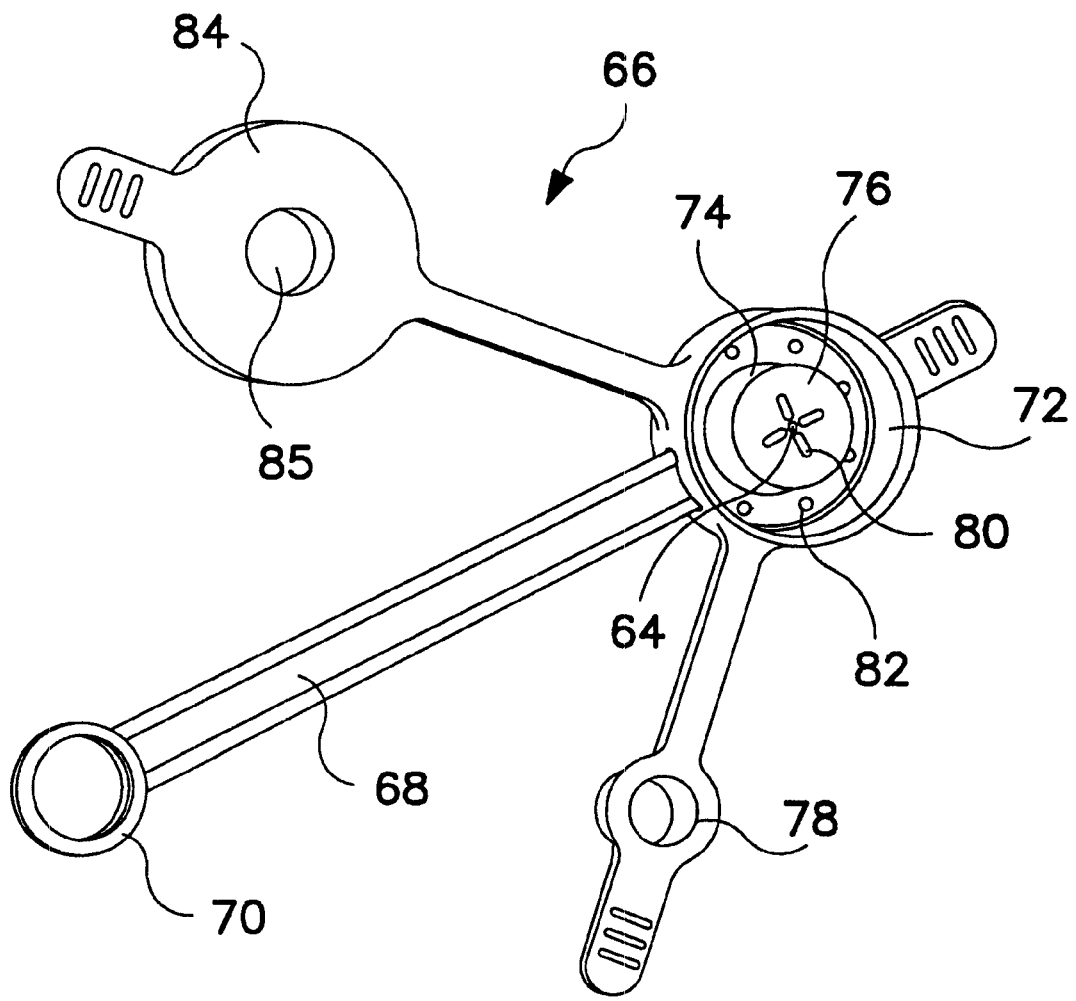
FIG. 7 is a perspective view of a cover member in accordance with the invention.

As mentioned, the first orifice 64 may be defined in the cover member. In the illustrated embodiments, the first orifice 64 is defined through a planar face 76 of a cylindrical extension 74. The cylindrical extension 74 extends into the fitting structure 12 so that the first orifice 64 is disposed generally opposite from and axially aligned with the catheter tube 34. As seen in FIG. 7, ribs 80 may be provided on the proximal side of the planar member 76 to ensure that the distal tip 42 of the catheter tube 34 does not seal against the planar member 76. As will be explained below, the turbulent flow is enhanced if the distal tip 42 is spaced from the first orifice 64.

Once the distal end portion 36 of the catheter tube 34 has been withdrawn into the cleaning chamber 62 and the cover member 66 is attached, a liquid such as a cleaning/lavage solution may be introduced into the chamber 62 by way of a conventional lavage port 22. In the illustrated embodiments, the lavage port 22 is in the collar 24 such that the lavage solution moves through the relatively narrow space 26 defined between the catheter tube 34 and collar 24. Also, the collar 24 serves to direct the cleaning solution along the outer circumference of the catheter tube 34. While the collar configuration is beneficial, it is still common to have secretions build up on the distal end portion 36 of the catheter tube 34. As discussed, such build up of mucous and secretions can be problematic and should be removed prior to subsequent use of the catheter assembly.

FIG. 4 conceptually illustrates what the applicants believe to be the turbulent flow conditions established by the method and apparatus according to the invention. Upon the distal end portion 36 of the catheter tube 34 being withdrawn into the cleaning chamber 62, the cover member 66 is attached to the distal end of the adaptor 14 to close off the cleaning chamber 62. The cylindrical extension 74 of the cover member 66 extends into the cleaning chamber 62 so that the orifice 64 is disposed opposite and spaced from the distal opening 38 of the catheter tube 34. The lavage/cleaning solution is introduced into the cleaning chamber 62 through a lavage port (not visible in FIG. 4). As discussed, the lavage port may be in the collar 24 so that the lavage/cleaning solution moves through the space 26. A suction is drawn at the proximal end of the catheter tube 34. This suction force serves to draw the lavage/cleaning solution into the distal opening 38 and establishes the turbulent air flow path. When suction is applied, a fluid medium other than the lavage/cleaning solution (in this case air) is drawn through the orifice 64 and into the distal opening 38 with the lavage/cleaning solution, as is illustrated by the arrows in FIG. 4. Although not wishing to be bound to any theory of operation, the applicants believe that a portion of the air and liquid mixture is then directed out the side or lateral openings 40 and travels along the outer circumferential surface of the catheter tube 34 and is drawn back into the distal opening 38. Thus, a continuous or circular flow path or pattern is established. It has been found that this pattern causes a significant turbulence in the lavage/cleaning solution around the outer circumference of the catheter tube 34. This turbulence greatly enhances the cleaning effect of the lavage/cleaning solution.

It should be appreciated that the size and orientation of the first orifice 64 may vary. It is preferred, however, that the first orifice 64 is generally directly opposite and axially aligned with the distal opening 38 of the catheter tube 34 to ensure that a metered amount of air is drawn directly into the distal opening 38. It is believed that the diameter of the first orifice 64 should be less than the diameter of the distal opening 38 but large enough to ensure that a sufficient amount of air is drawn into the catheter tube for establishing the turbulent air flow path.

In the embodiment of FIG. 4, the fluid medium (air) is drawn into the cleaning chamber 62 by the suction force being applied at the proximal end of the catheter tube 34. It should be understood that a pressurized source of air or other fluid medium may be used to establish the turbulent flow path. This pressurized source may be in addition to or in place of the suction force. It should also be appreciated that the lavage/cleaning solution may be introduced into and removed from the cleaning chamber by any number of different arrangements. For example, a separate suction port may be provided in the cleaning chamber for removing the lavage/cleaning solution.

The turbulent flow path is defined longitudinally between the side or lateral openings 40 and the distal end opening 38. Accordingly, a plurality of side openings 40 may be defined in the distal end portion 36 of the catheter tube 34. The number and size of the openings should not be so great to cause dilution of the amount of air in the turbulent air flow path.

FIGS. 5 and 6 illustrate an alternative embodiment incorporating an internal cover member 86. With this type of arrangement, it is not necessary to remove the adaptor 14 from the patient's artificial airway in order to conduct the cleaning operations. As the catheter tube is withdrawn by the clinician into the adaptor 14, the internal cover member 86 automatically moves to a sealing or closing position upon the catheter being moved past the cover member 86. For example, in the embodiment of FIG. 6, the catheter tube 34 is withdrawn into the collar 24. Once the distal tip 42 of the catheter tube 34 is withdrawn past the cover member 86, the cover member moves into engagement against the distal end of the collar 24. The cleaning chamber is thus established within the collar 24 and includes the space between the distal tip 42 of the catheter tube 34 and the cover member 86, as well as the longitudinal space 26 defined between the catheter tube 34 and collar 24.

In the illustrated embodiment, the internal cover member 86 comprises a hinged flapper valve 90 mounted in a valve ring 88 carried in the adaptor 14. Flapper valve 90 includes a hinge 92 that allows the flapper valve 90 to move between its open and closed positions. Although not particularly illustrated in the cross-sectional view of FIG. 6, it should be understood that the first orifice 64 is defined through the flapper valve 90, for example in the center of ribs 94, so as to be generally axially aligned with distal opening 38.

It should be appreciated that any manner of automatically closing internal cover members may be utilized to define a closed cleaning chamber upon withdraw of the catheter tube. The embodiment illustrated in FIGS. 5 and 6 is particularly useful in a closed suction respiratory catheter assembly. Various other internal valve or cover members are described in detail in co-pending and commonly owned U.S. patent application Ser. Nos. 09/157,605 and 09/357,591. The '605 and '591 applications are incorporated herein in their entirety for all purposes.

Operation of the embodiment shown in FIGS. 5 and 6 is essentially the same as that described above. Once the catheter tube 34 is withdrawn into the collar 24, a lavage/cleaning solution is introduced into the collar 24 while a suction is drawn through the catheter tube 34. The suction force also tends to draw the flapper valve 90 into sealing engagement against the distal end of the collar 24. The turbulent flow path is established by a metered amount of air being drawn through the first orifice 64 defined in the flapper valve 90, into the distal opening 38 of the catheter tube, out the side or lateral openings 40 along with a portion of the lavage/cleaning solution, and back into the distal opening 38. Due to the fact that the space 26 between the collar 24 and the catheter tube 34 is relatively narrow, the turbulent flow is particularly concentrated in this area resulting in a significantly enhanced cleaning effect of the distal end portion 36 of the catheter tube 34.

A plurality of rib-like structures 94 may be provided on the flapper valve 90 to prevent the distal tip 42 of the catheter tube 34 from completely sealing against the flapper valve, a condition that would cause the turbulent flow to cease. The ribs 94 also reduce surface area contact between the flapper valve 90 and catheter tube 34 as the tube is withdrawn from the patient, thereby minimizing mucous/secretion build-up on the flapper valve 90.

Applicants have found that in certain embodiments of the apparatus according to the invention wherein the cleaning chamber 62 is relatively large, for example in the embodiments of FIGS. 1, 3, and 4, some of the lavage/cleaning solution may remain in the cleaning chamber 62 after the cleaning operation. In certain situations, it may be desired to remove this solution before the catheter assembly is used again.

To remove any remaining lavage/cleaning solution from the cleaning chamber 62, additional orifices 82 may be provided in the chamber. These orifices 82 are disposed and oriented so that air drawn in through the orifices 82 is directed generally against the inner circumferential wall of the cleaning chamber 62 to force the cleaning/lavage solution radially inward towards the suction catheter to be suctioned through the catheter tube 34.

The additional orifices 82 may be provided in any defining member of the cleaning chamber 62. In the illustrated embodiments, the additional orifices 82 are disposed in the cover member 66 and are arranged in a circular pattern around the first orifice 64. A cap ring 84 is also provided with the cover member 66 to isolate or cover the additional orifices 82. The cap ring 84 has a central aperture 85 that is aligned with the first orifice 64 so that air can be drawn in through the first orifice 64 while the additional orifices 82 remained cover. A plug member 78 is also provided with cover member 66 to isolate or cover the first orifice 64. Plug member 78 may be inserted through the orifice 85 in the cap ring 84 in order to completely isolate or seal the distal end of the adaptor 14 or other structure that defines the cleaning chamber 62.

In operation, the clinician would remove plug member 78 during the turbulent flow cleaning operation. After a sufficient period of time for cleaning the distal end portion 36 of the catheter tube 34 as described above, the clinician would then remove the cap ring 84. Once the cap ring 84 is removed, air is also drawn in through the additional orifices 82 in a circular pattern around the first orifice 64. This additional air flow results in the cleaning/lavage solution being directed radially inward towards the distal tip 42 and side or lateral openings 40 so that the solution may be completely removed from within the cleaning chamber 62. Once the entire process is complete, the cap ring 84 and plug member 78 may be used to seal or cover the distal opening of the adaptor 14 until the catheter assembly 10 is needed again.

While the invention has been described in detail with respect to specific embodiments thereof, those skilled in the art, upon obtaining an understanding of the invention, may readily conceive of alterations to, variations of, and equivalents to the described embodiments. It is intended that the present invention include such modifications and variations as come within the scope of the appended claims and their equivalents.

What is claimed is:

1. A method for cleaning a catheter tube wherein a distal end portion of the catheter tube includes a distal tip having a distal opening and at least one side opening adjacent to the distal tip, said method comprising:

withdrawing the catheter tube into a cleaning chamber until the distal end portion of the catheter tube is disposed within the cleaning chamber;

closing the cleaning chamber with a cover member disposed generally opposite from the distal tip;

injecting a cleaning solution into the cleaning chamber;

applying suction to the cleaning chamber through the catheter tube;

drawing air into the distal opening of the catheter through an orifice in the cover member during said suctioning; and wherein a turbulent flow path is created within the cleaning chamber that enhances the cleaning operation.

2. The method as in claim 1, comprising disposing the distal opening in the catheter tube in axial alignment with the orifice in the cover member.

3. The method as in claim 2, comprising disposing the distal tip of the catheter tube spaced from the cover member.

4. The method as in claim 1, wherein after a period of time of supplying air into the cleaning chamber through the orifice in the cover member, said method further comprises supplying air into the cleaning chamber from additional orifices disposed so as to urge the cleaning solution away from sides of the cleaning chamber.

5. The method as in claim 4, comprising defining the additional orifices in the cover member arranged around the first orifice.

6. The method as in claim 1, comprising supplying the air through the first orifice in the cover member by reducing pressure in the cleaning chamber.

7. The method as in claim 1, comprising supplying the air through the first orifice in the cover member by pressurizing the air drawn through the cover member.

8. The method as in claim 1, wherein the catheter tube is a respiratory suction catheter tube, said method used to clean mucous and secretions form the distal end portion of the catheter tube.

9. The method as in claim 1, wherein the cleaning chamber is defined at least in part by a fitting having a port in communication with a patient's artificial airway, said step of closing the cleaning chamber with the cover member comprising removing the fitting from the artificial airway and closing off the port with the cover member.

10. The method as in claim 1, wherein the cleaning chamber is defined within a portion of a fitting that is automatically closed off by the cover member upon withdrawing the distal end portion of the catheter tube past the cover member and into the fitting portion.

11. A method of creating a turbulent flow at a distal end of a medical device tube having a distal opening and at least one side opening adjacent to the distal opening, said method comprising the steps of:

disposing the distal end of the tube in a closed chamber such that the distal opening is generally opposite from a first orifice defined through the chamber;

introducing a liquid into the chamber;

drawing the liquid into the distal opening in the tube; and drawing a fluid medium through the first orifice defined in the chamber and into the distal opening in the tube with the liquid;

conveying a portion of the fluid medium and liquid mixture out the side opening in the tube, and back into the distal opening in the tube in a flow pattern;

wherein the flow pattern creates a turbulence in the liquid flowing around the distal end of the tube within the chamber.

12. The method as in claim 11, wherein the medical device tube is a catheter tube, said disposing step comprising withdrawing the distal end of the catheter tube into a distal fitting member of a catheter assembly.

13. The method as in claim 12, further comprising covering a portion of the fitting with a cover member to define the chamber, the cover member having the first orifice defined therethrough.

14. The method as in claim 12, wherein the catheter tube is a respiratory suction catheter tube, said method used to clean the distal end of the suction catheter tube.

15. The method as in claim 11, wherein said drawing a fluid medium step comprises drawing air through the first orifice.

16. The method as in claim 15, comprising creating a reduced pressure with the chamber to draw the air through the first orifice.

17. The method as in claim 16, comprising drawing a suction through the tube.

18. The method as in claim 11, further comprising drawing a fluid medium through additional orifices in the chamber oriented so as to direct the fluid medium around the circumference of the tube in the chamber.

19. The method as in claim 18, comprising drawing air through the additional orifices.

20. A catheter tube assembly comprising:

a catheter tube having a distal opening and at least one side opening defined in a distal end portion of said catheter tube adjacent to said distal opening, said distal opening and said side opening being configured for and in communication such that a portion of cleaning solution or air drawn into said distal opening is transferred and exited from said side opening, said catheter tube configured to receive a suction force therethrough;

a cleaning chamber, said distal end portion of said catheter tube movable into said cleaning chamber, said cleaning chamber configured to accommodate said catheter tube such that turbulent flow is present during cleaning of said catheter tube;

a port in communication with said cleaning chamber for introducing the cleaning solution into said chamber;

a first orifice defined through said cleaning chamber and disposed so as to be generally opposite said distal opening of said catheter tube upon withdrawing said distal end portion into said chamber, said first orifice configured for receiving air and having air transported therethrough by the suction force applied to said catheter tube; and at least one projection defined in said cleaning chamber and configured to define a distance between said first orifice and said distal opening of said catheter tube such that said first orifice and said distal opening of said catheter tube remain separated.

21. The catheter tube assembly as in claim 20, further comprising a fitting through which said catheter tube passes, said cleaning chamber defined at least in part by said fitting.

22. The catheter tube assembly as in claim 21, further comprising a cover member associated with said fitting, said cover member closing off said cleaning chamber upon said distal end of said catheter tube being withdrawn into said fitting, said orifice and said projection defined in said cover member.

23. The catheter tube assembly as in claim 22, wherein said fitting comprises a port that is detachable from a patient's artificial airway, said cover member configured to close off said port upon detaching said fitting to define said cleaning chamber.

24. The catheter tube assembly as in claim 23, wherein said cover member is removable from said fitting.

25. The catheter tube assembly as in claim 22, wherein said cover member is disposed within said fitting and automatically moves to closes off said cleaning chamber upon said distal end of said catheter tube being withdrawn past said cover member.

26. The catheter tube assembly as in claim 25, wherein said cover member comprises a flap member.

27. The catheter tube assembly as in claim 20, wherein said distal end of said catheter tube having a circumference, and further comprising at least one additional orifice in said cleaning chamber disposed so as to direct air generally along said circumference of said distal end of said catheter tube within said cleaning chamber.

28. The catheter tube assembly as in claim 20, wherein said catheter tube is a respiratory suction catheter tube.

29. The catheter tube assembly as in claim 28, further comprising a fitting connectable with a patient's artificial airway, said cleaning chamber defined at least in part by said fitting.

30. The catheter tube assembly as in claim 29, wherein said fitting comprises a port detachable from the artificial airway, and further comprising a cover member configured to close off said port to define said cleaning chamber, said first orifice defined in said cover member.

31. The catheter tube assembly as in claim 29, further comprising a cover member disposed within said fitting, said cover member automatically movable to a position to define and close off said cleaning chamber upon said distal end of said catheter tube being withdrawn past said cover member, said first orifice defined in said cover member.

32. The catheter tube assembly as in claim 31, wherein said cover member is a hinged flap member.

33. A catheter tube assembly comprising:

a catheter tube having a distal opening and at least one side opening defined in a distal end portion of said catheter tube adjacent to said distal opening;

a cleaning chamber, said distal end portion of said catheter tube movable into said cleaning chamber;

a port in communication with said cleaning chamber for introducing a cleaning solution into said chamber;

a first orifice defined through said cleaning chamber and disposed so as to be generally opposite said distal opening of said catheter tube upon withdrawing said distal end portion into said chamber;

wherein upon applying a suction force through said catheter tube a turbulent flow pattern is established by air drawn through said first orifice and into said distal opening of said catheter tube with the cleaning solution, a potion of the air and cleaning solution mixture being conveyed out said side opening, and back into said distal opening thereby creating a turbulence in said cleaning solution within said cleaning chamber;

said cleaning chamber having at least one additional orifice disposed therein so as to direct air generally along a circumference of said distal end of said catheter tube within said cleaning chamber; and a plurality of said additional orifices disposed around said first orifice.

34. A catheter tube assembly comprising:

a catheter tube having a distal opening and at least one side opening defined in a distal end portion of said catheter tube adjacent to said distal opening;

a cleaning chamber, said distal end portion of said catheter tube movable into said cleaning chamber;

a port in communication with said cleaning chamber for introducing a cleaning solution into said chamber;

a first orifice defined through said cleaning chamber and disposed so as to be generally opposite said distal opening of said catheter tube upon withdrawing said distal end portion into said chamber;

wherein upon applying a suction force through said catheter tube a turbulent flow pattern is established by air drawn through said first orifice and into said distal opening of said catheter tube with the cleaning solution, a potion of the air and cleaning solution mixture being conveyed out said side opening, and back into said distal opening thereby creating a turbulence in said cleaning solution within said cleaning chamber;

said cleaning chamber having at least additional orifice disposed therein so as to direct air generally along a circumference of said distal end of said catheter tube within said cleaning chamber;

a plurality of said additional orifices disposed around said first orifice; and a cover member movable to a position to close off said cleaning chamber upon said distal end of said catheter tube being withdrawn into said cleaning chamber, said first orifice and said additional orifices defined through said cover member.

* * * * *